United States Patent [19]

Vletter

[11] Patent Number: Plant 7,100

[45] Date of Patent: Jan. 9, 1990

[54] LILY PLANT NAMED AVIGNON

[75] Inventor: Floris Vletter, Rijnsburg, Netherlands

[73] Assignee: Gebr. Vletter & J.A. den Haan, Netherlands

[21] Appl. No.: 261,251

[22] Filed: Oct. 24, 1988

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new lily plant named Avignon particularly characterized by its brownish red flower coloring and good forcing.

1 Drawing Sheet

The present invention comprises a new and distinct cultivar of lily, botanically known as Lilium (Asiatic hybrid), and hereinafter referred to by the cultivar name Avignon.

Avignon is a product of a planned breeding program which had the objective of creating new lily cultivars with better forcing properties.

Avignon was originated by me from a hybridization made in a controlled breeding program in Rijnsburg, The Netherlands beginning in 1980. The female parent was the variety known as Eurovision and the male parent of Avignon was an unknown, unpatented seedling.

Avignon was discovered and selected by me as one flowering plant within the progeny of the stated cross in June 1982 in a controlled environment in Rijnsburg, The Netherlands.

I accomplished the first act of asexual reproduction of Avignon by scaling bulbs of the initial selection in August 1982 in a controlled environment in Rijnsburg. Horticultural examination of selected units initiated in 1984 has demonstrated that the combination of characteristics as herein disclosed for Avignon are firmly fixed and are retained through successive generations of asexual reproduction.

In describing the characteristics of the variety, the guidelines for the species Lilium promulgated by the International Union for the Protection of New Varieties of Plants (UPOV) have been applied. These descriptors appear in parantheses in the detailed description of the characteristics of the variety. The specific dimensions of the various parts of the plant depend on the circumstances of growing (for example, light intensity).

Avignon has not been observed under all possible environmental conditions. The phenotype may vary significantly with variations in environment such as temperature, light intensity, and day length. The following observations, measurements, and comparisons describe plants grown in Wageningen, The Netherlands under greenhouse conditions which approximate those generally used in commercial practice.

The following traits have been repeatedly observed and are determined to be basic characteristics of Avignon which in combination distinguish this lily as a new and distinct cultivar.

1. The particular orange red color of Avignon.
2. Good forcing characteristics with a short forcing-time.

3. Medium long and medium wide flower structure, with branches at an angle of about 70° with the peduncle.
4. Narrow honey gland, thick with transparent white gland hairs.

The accompanying photographic drawing shows typical flower characteristics of Avignon, with colors being as true as possible with illustrations of this type.

In the following description, color references are made to The Royal Horticultural Society Colour Chart (RHS).

Origin: Seedling.
Name: Avignon.
Parentage:
*Female parent.*—Eurovision.
*Male parent.*—Unknown seedling.
Classification: Asian hybrid.
Plant:

1. *Plant height (on opening of the anthers of the first flower).*—Medium (5).
2. *Stalk.*—Anthocyanin coloring—present, middle to strong, at basis very strong. (9). Color: middle green. Growth of Hair: present, very weak (9). Type of coat of hair: long (2). Division of coat of hair: especially in leaf axils, only at the top (1). Internode length: at basis longer, slightly (3). Cross section: ribbed (3). Bulbils: present, lacking at basis (9). Color of the bulbils: brown, with hint of light green (1).
3. *Leaf.*—Position: spread out (2). Top angle of the base with the stalk: sharp, about 45° (1). Length: medium (5). Width: medium (5). Thickness: normal (2). Form (middle third part of the stalk): narrow elliptic (1). Color of the top: dark green (7). Luster of the top: strong (7). Growth of hair at the bottom: lacking (1). Top: pointed (2). Curve of the edge: lacking (1). Membraneous edge: lacking (1). Indentation of the edge: lacking (1). Uniformity: present (9). Form in cross section: level (1). Top part: straight (5). Flexibility: strong (7). Stalk: lacking (1).

Flower:

1. *Structure.*—Type: raceme (1). Secondary flowers: present (9). Growth of hair: present, very weak, in leaf axils and on high leaves (9). Bracts: present (9). Number of bracts in comparison with the number of primary flowers: equal (1). Bracteole: present (9). Number of bracteoles in comparison with the total number of flowers: equal (1). Position: erect (3). Type: bowl-shaped (3). Cross-section: medium (5). Height of crown: medium (5). Length of longest flower stalk: medium (5).

2. *Petal.*—Length of longest exterior petal: medium (5). Width of widest exterior petal: medium (5). Length of longest interior petal: medium (5). Width of widest interior petal: medium (5). Color of the inside of the interior petal: approximately 34A to near 34B; base 34B. Color of the outside of the interior petal: near 169A, but slightly darker, medium slightly paler; middle nerve brownish red with hint of green. Color of the inside of the exterior petal: 34A tinged with a darker 179A; base lighter, near 34B. Color of the outside of the exterior petal: a good showing of both 171A and 34A; with distal having a hint of purple; edges orange-red, near 34A, top slightly thickened and green. Marking on the inside: hardly present; only on interior petals. (9). Color of the marking: dark brown. Type of marking on the inside: spots, elliptic; approximately $1 \times \frac{3}{4}$ mm. (1). Density of the spots in the marking: very thin. (1). Color of the inside of the throat: near 180C. Color of the outside of the throat: near 179B to 178C. Surface structure of the inside: ribbed and papillate, honey gland about 20 mm long. (4). Luster at the inside: lacking. (1). Curve of the edges of the petal: present. (9). Type of curse of the edge of the petals: rough. (2). Flexure of petals: present. (9). Bended part of the petals: distal part. (2). Extent of bending: medium. (5). Fragrance: lacking. (1).

Reproductive organs:

*Length of stamina.*—medium. (5).

*Color of the filaments.*—Orange-red, lighter at base.

*Color of the anthers.*—Brownish purple (unripe).

*Color of pollen.*—Dark brown. (4).

*Length of the pistil.*—Medium. (5).

*Color of the style.*—Brownish orange-red.

*Color of the stigma.*—Purple, reddish purple gland hairs. (2).

Bulb:

*Type (in period of rest).*—Type 2.

*Top.*—Pointed. (1).

*Density of scales.*—Close. (7).

*Color of the exterior scales.*—White. (1).

*Top of the scales.*—Pointed. (1).

*Underground part of the stalk.*—Bulbils — present. (9). Roots — present. (9).

I claim:

1. A new and distinct cultivar of lily plant named Avignon, substantially as shown and described.

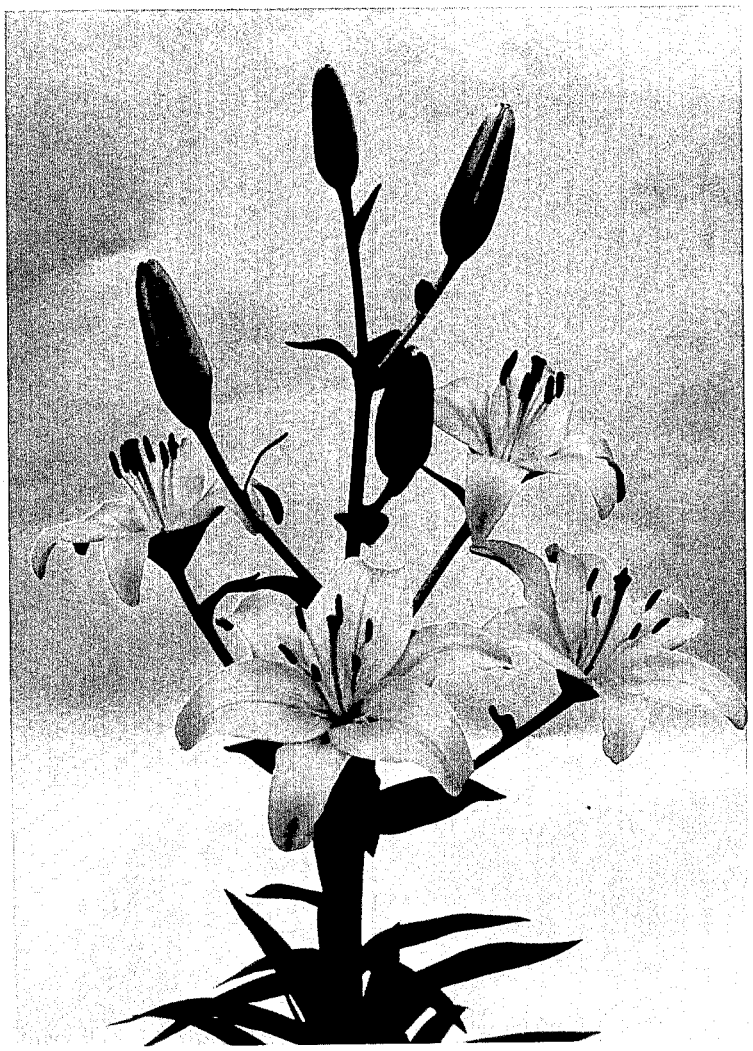

* * * * *